(12) United States Patent
Greer et al.

(10) Patent No.: US 9,448,112 B2
(45) Date of Patent: Sep. 20, 2016

(54) MULTIFUNCTIONAL FLUID METER AND METHOD FOR MEASURING COOLANT, BIO-DIESEL, GAS-ETHANOL AND DEF

(71) Applicant: Spectro Scientific, Inc., Chelmsford, MA (US)

(72) Inventors: James Greer, Grafton, MA (US); Robert J. Guthrie, Lowell, MA (US); John Coates, Newtown, CT (US)

(73) Assignee: Spectro Scientific, Inc., Chelmsford, MA (US)

( * ) Notice: Subject to any disclaimer, the term of this patent is extended or adjusted under 35 U.S.C. 154(b) by 0 days.

(21) Appl. No.: 13/931,091

(22) Filed: Jun. 28, 2013

(65) Prior Publication Data

US 2014/0002809 A1    Jan. 2, 2014

Related U.S. Application Data

(60) Provisional application No. 61/666,446, filed on Jun. 29, 2012.

(51) Int. Cl.
*G01N 21/00* (2006.01)
*G01J 3/42* (2006.01)
(Continued)

(52) U.S. Cl.
CPC ............. *G01J 3/42* (2013.01); *G01J 3/027* (2013.01); *G01J 3/0218* (2013.01); *G01J 3/0264* (2013.01);
(Continued)

(58) Field of Classification Search
CPC ........ G01J 3/42; G01J 3/0218; G01J 3/0264; G01J 3/027; G01J 3/0291; G01J 3/0294; G01J 3/10; G01J 3/427; G01N 21/031; G01N 21/255
See application file for complete search history.

(56) References Cited

U.S. PATENT DOCUMENTS

| 4,076,420 A | * | 2/1978 | De Maeyer | ........ G01N 21/272 356/246 |
| 6,342,948 B1 | * | 1/2002 | Gilby | ................ G01N 21/0303 356/246 |

(Continued)

FOREIGN PATENT DOCUMENTS

| RU | 6630 U1 | 5/1998 |
| RU | 6561 U1 | 8/2007 |
| WO | 00/09985 A2 | 2/2000 |

OTHER PUBLICATIONS

International Search Report dated Oct. 31, 2013 from corresponding PCT/US2013/048658, 3 pages.
Written Opinion dated Oct. 31, 2013 from corresponding PCT/US2013/048658, 3 pages.
European Search Report mailed Mar. 14, 2016 in European Patent Application No. 13810440.1 (nine (9) total pages).

*Primary Examiner* — Kara E Geisel
*Assistant Examiner* — Hina F Ayub
(74) *Attorney, Agent, or Firm* — Iandiorio Teska & Coleman, LLP (57) ABSTRACT

A simple and compact apparatus, and a method, for determining the characteristics of a number of fluids used in the truck and automotive industries including coolant, bio-diesel, gas-ethanol and diesel engine fluid (DEF). The apparatus includes a sample container providing optical paths of different lengths for making measurements on a sample. The dual path length design allows the apparatus to capture both NIR and UV spectral ranges. The qualitative and quantitative properties of the fluid under test are compared to test results under normal conditions or to the properties of unused fluid. Two light sources are used within a spectrometer with each source being associated with a different optical path length.

9 Claims, 7 Drawing Sheets

(51) Int. Cl.
  *G01J 3/02*       (2006.01)
  *G01J 3/10*       (2006.01)
  *G01J 3/427*      (2006.01)
  *G01N 21/03*      (2006.01)
  *G01N 21/31*      (2006.01)
  *G01N 21/3577*    (2014.01)
  *G01N 21/33*      (2006.01)

(52) U.S. Cl.
  CPC ............ *G01J 3/0291* (2013.01); *G01J 3/0294* (2013.01); *G01J 3/10* (2013.01); *G01J 3/427* (2013.01); *G01N 21/0303* (2013.01); *G01N 21/31* (2013.01); *G01N 21/33* (2013.01); *G01N 21/3577* (2013.01); *G01J 2003/106* (2013.01)

(56) References Cited

U.S. PATENT DOCUMENTS

| | | | | |
|---|---|---|---|---|
| 8,531,671 | B1* | 9/2013 | Hansen | 356/438 |
| 8,885,913 | B2* | 11/2014 | Basiji | G01N 33/57492 356/326 |
| 2006/0246594 | A1* | 11/2006 | Appel | G01N 21/6408 436/81 |
| 2008/0272303 | A1 | 11/2008 | Chu et al. | |
| 2010/0134794 | A1* | 6/2010 | Odegard et al. | 356/301 |
| 2010/0231904 | A1* | 9/2010 | Tyrie | G01N 1/14 356/319 |
| 2010/0305827 | A1 | 12/2010 | Fournel et al. | |
| 2012/0223515 | A1* | 9/2012 | Avramescu et al. | 280/830 |
| 2014/0043044 | A1* | 2/2014 | Parker et al. | 324/633 |

* cited by examiner

Simplified Schematic and Functional Block Diagram

Rules – Coolant Analysis

OSA4 CoolCheck™ report recommendations
All Normal -----

Analysis indicates proper performance of the cooling system. Resample at normal interval

If Glycol Content Less Than 35 (<35) and Greater Than (>10) ----

Glycol level too low to provide proper protection from overheating and / or freezing. Recommend glycol/water mix of 50/50.

If Glycol Content is Less Than (<10) ----

Glycol level too low to provide proper protection from overheating and / or freezing. Recommend flushing and filling system with proper coolant 50/50% mixture.

If Glycol Content Greater Than (>65) ------

Glycol level is too high. Recommend glycol/water mix of 50/50%.

If Nitrites are Less Than (<300) -----

Nitrite level below 300 ppm. If sample is nitrite-free coolant, then no action recommended. If coolant is nitrite based, add nitrite additive package (Supplemental Coolant Additive (SCA)) based on manufacturer recommendation or drain and refill with proper 50/50% mixture.

If Clarity - Hazy or Contamination - Moderate ------

Indicates particulate contamination or beginning of system corrosion – monitor system and resample at half interval.

If Clarity – Cloudy, or Opaque, or Contamination -Heavy ------

Indicates particulate contamination, deposits forming, product mixing or excessive system corrosion. Recommend flushing and filling system with proper 50/50% coolant mixture.

Fig. 10

A---- Unit ID – Identifier for vehicle that is entered during sample data entry
B---- Sample Date - Date and time that the sample was processed
C---- Sample ID - Serial number followed by sample number 1---- Type – Designates ELC or Conventional coolant (Unknown can indicate a mixture)
2---- Clarity – Designates the Visual appearance of sample (Clear, Hazy, Cloudy, Opaque)
3---- Contamination – Designates any outside contamination (Normal = Trace, Abnormal = Moderate, Severe = Heavy)
4---- Color – Signifies the color of the coolant. Can indicate a mixture or excessive contaminates.
5---- Freeze Point – Lowest temperature before antifreeze will freeze
6---- Glycol Content – Percentage of Water and Glycol mixture in the coolant (50/50% is ideal)
7---- Boil Point – Highest temperature before coolant begins to overheat
8---- Nitrites – Indication of nitrite based SCA (Supplemental Coolant Additive) left in the coolant. Normal trip levels are less than 300 ppm which indicates additives are depleted. Too much nitrites can also be a problem (monitor based on manufacturers recommendation)
9---- Key that shows what is indicated in the GRADE column

Fig. 11

MULTIFUNCTIONAL FLUID METER AND METHOD FOR MEASURING COOLANT, BIO-DIESEL, GAS-ETHANOL AND DEF

This application claims priority from and the benefit of provisional application Ser. No. 61/666,446 filed on Jun. 29, 2012, the entire contents of which are incorporated herein by reference, for all purposes.

BACKGROUND OF THE DISCLOSURE

1. Field of the Disclosure

The present disclosure relates to a new apparatus and method for evaluating the condition (i.e. the measurement of properties) of coolant and characteristics and analyses of fuel quality (gasoline-ethanol and bio-diesel) and DEF (diesel engine fluid-urea solution) quality. More particularly, it relates to those apparatus and methods for doing so spectroscopically.

2. Background Art

Fluid integrity is one of the most important issues in the engine maintenance and condition monitoring. Coolant, fuel, and the urea solutions used in diesel engine fluids are all critical.

Coolants

Nearly all engines use coolants with similar base fluids: a 50/50 mix of ethylene glycol and water. In some circumstances, industrial engines may utilize other base fluids, such as atomized water or a mixture of propylene glycol and water. In addition to the base fluid, there are a small amount of other ingredients including corrosion inhibitors, antifoam agents, dyes and other additives. While these other ingredients make up only a small fraction of the overall coolant, they are what differentiate one coolant from another.

Diverse technologies have been developed to protect engines from corrosion. In Europe, problems with hard water minerals forced coolant technologies to be phosphate-free. Calcium and magnesium, minerals found in hard water, react with phosphate inhibitors to form calcium or magnesium phosphate, which typically leads to scale formation on hot engine surfaces. This could lead to loss of heat transfer or corrosion under the scale. To replace phosphates, conventional European coolants contain a mix of inorganic oxides like silicates and inhibitors called carboxylates. Carboxylates provide corrosion protection by chemically interacting at the metallic corrosion sites, rather than by forming a layer of inhibitors that cover the total surface. The mix of carboxylates and silicates is also called a hybrid technology because it is a mix of conventional inorganic technology and fully carboxylate or organic technology.

In Asia, there is a ban on coolants containing silicate. To provide protection, most coolants contain a mix of carboxylates and inorganic inhibitors such as phosphates.

These coolants can also be considered hybrids, but they are distinct from the European hybrids due to the lack of silicates.

Extended-life carboxylate-based coolants were developed to be globally acceptable and provide superior performance over existing technologies. This technology is also known as organic additive technology (OATs). Because full carboxylate coolants have no silicates, they meet the stringent requirements of the Asian specifications. They also meet the European coolant requirements because they have no phosphates. These coolants have developed international popularity due to having an unsurpassed corrosion protection for extended time intervals.

In general, coolants degrade over time as the ethylene glycol breaks down into primarily glycolic and formic acids. Degradation occurs more quickly in engines operating at higher temperatures or those that allow more air into cooling systems.

Currently techniques and methods available for routinely detecting and quantifying the quality of coolant is to use test strips.

Another test is to check for nitrite and molybdate corrosion inhibitors in the coolant. Most conventional coolants require either continual supplemental coolant additions (SCAs) or lab analysis to ensure proper performance.

Various inhibitors, such as nitrites and molybdates, are easily monitored using test strips. Because nitrites deplete rapidly compared to other inhibitors, testing for nitrite allows one to learn the coolant's nitrite level, but nothing else. Therefore a new testing apparatus and test method was sought out.

Some engines require inhibitors such as nitrites to be maintained at certain levels to offer protection against cavitation corrosion, which can occur in engines with removable cylinder liners. Nitrites tend to deplete rapidly in conventional coolants and must be replenished at regular intervals. Carboxylate-based ELC coolants typically have lower nitrite depletion levels because the carboxylates provide the required cavitation protection and therefore much longer preventive maintenance intervals.

Some common cause of coolant failure are debris (including rust), leaking heaters, plugged heater (or other restrictions in system), system overheating, electrolysis (unacceptably high voltage in the coolant) which results in degradation of hoses or heater, and improper concentration (mix ratio with water).

Bio-Diesel Fuel Quality

In comparison to other alternative fuels, there are a number of unique qualities and properties of biodiesel fuel. What makes a fuel different from others are its cetane number and heat of combustion. The viscosity of a fuel is important because it influences the atomization of the fuel being inserted into the engine combustion chamber. Whereas biodiesel fuel property has a viscosity much closer to diesel fuel than vegetable oil, it helps create a much lower drop, which burns cleaner.

Another main property of biodiesel fuel is its lubricating properties. It has much better lubricating properties and a higher cetane ratings than today's lower sulfur diesel fuels. Biodiesel also helps in reducing fuel system wear. The fuel injection equipment depends on the fuel for its lubrication. The biodiesel fuel properties increase the life of the fuel injection equipment. Giving better lubricity, a more complete combustion and an increase in the engine energy output, partially compensates for the lower energy density of biodiesel fuel as compared to petrodiesel.

The physical properties of biodiesel fuel include, the possibility of being different in color, from golden and dark brown, all depending on the production feedstock. It is immiscible with water, has a high boiling point and low vapor pressure. The flash point of biodiesel is considerably higher than that of petroleum diesel. Biodiesel fuel has a density of ~0.88 g/cm$^3$, which is less than that of water. It has practically no sulfur content, and is frequently used as an additive to Ultra-Low Sulfur Diesel (ULSD) fuel. Biodiesel fuel has an effect on copper-based materials, and as well on zinc, tin, lead, and cast iron. However, the stainless steels and aluminum are not affected by bio fuel. Biodiesel fuel properties also have an effect on some types of natural rubbers found in some older engine components. However, the frequently used synthetic rubbers FKM-GBL-S and FKM-GF-S found in current vehicles are found to handle biodiesel under virtually all conditions.

Gas-Ethanol Quality

When fuel contains more than 10 percent ethanol, problems can arise in a vehicle, including engine stalling, failed starting and difficulty accelerating. It can also decrease the life of the engine. Because fuel station owners are not required to test the levels of ethanol in the fuel delivered, and car owners do not become aware of the problem until damage has been done, it is important to test the levels of ethanol in the fuel being used.

Using the characteristic spectral components of materials, the new apparatus for multifunctional fluid meter and method for measuring coolant, bio-diesel, gas-ethanol and diesel engine fluid (DEF) will be able to measure and report the following gas-ethanol properties; specifically the percentage of ethanol in gasoline.

DEF (Diesel Exhaust Fluid) Quality

DEF is a high purity solution of 32.5% urea in deionized water. Urea is a colorless, odorless, non-hazardous, non-flammable, non-combustible crystalline solid made from natural gas, with a molecular weight of 60 and molecular formula of $(NH_2)_2CO$.

DEF is used to convert noxious NOx into harmless nitrogen gas.

In 2000 and 2001, the EPA mandated tougher emission control standards to be phased in for all on-highway vehicles. Effective Jan. 1, 2010, all new on-road vehicles sold must meet the emission standard of 0.2 grams of nitrogen oxide (NOx) per brake horsepower-hour. Vehicle and engine manufacturers have developed Selective Catalytic Reduction (SCR) technology, which uses DEF to convert noxious NOx into harmless nitrogen gas, which makes up 80% of the air we breathe. Industry projections on SCR acceptance vary: 90% of heavy duty trucks, beginning in 2010, are expected to use SCR, while 50-75% of diesel cars and light duty vehicles are expected to use SCR technology. Auto and truck makers have invested significant time and resources to develop the technology and have developed a set of internationally accepted standards—ISO22241—for the production and use of DEF. If these standards are not met, there is a serious risk of poisoning the catalyst used in the vehicle mounted SCR system.

Most cars and light duty trucks will have 5-7 gallon on-vehicle tanks to store DEF, while heavy duty trucks will have 10-30 gallon tanks. This DEF is metered by the on-board computer into the exhaust gas at rates required to meet the tailpipe NOx standards.

Based on the following assumptions for the light duty market—7-gallon DEF tank, 20 miles per gallon of diesel, 2-4 gallons of DEF per 100 gallons of diesel—a car or pickup truck owner will likely need to fill the DEF tank every 3,500-7,000 miles, or about the interval between oil changes. So, it is likely that most car and light duty owners will have the DEF tank topped off during oil change services.

For heavy duty vehicles—18 gallon DEF tank, 6 miles per gallon of diesel, 2-4 gallons of DEF per 100 gallons of diesel—a truck owner will likely need to fill the DEF tank every 2,700-5,400 miles, which is much more frequent than for cars and light duty trucks. So, it's likely that most heavy duty trucks will top off DEF tanks during every second or third fuel fills.

In view of all of the above requirements, a device for on-site measurement of fluid characteristic integrity is desired. Further, such a device should be compact, cost effective, easy to operate and provide reliable results.

SUMMARY OF THE DISCLOSURE

It is an object of this disclosure to provide a simple and compact apparatus for determining the characteristics of a number of fluids used in the truck and automotive industries.

It is a further object of the disclosure to provide a sample container providing optical paths of different lengths for making measurements on a sample.

It is another object of the disclosure to provide a dual path length spectrometer for making measurements in the visual (VIS) range of 200 nm-750 nm and the near infared (NIR) range of 750 nm-1100 nm.

Using the characteristic spectral components of materials, the disclosure is directed to an apparatus useable as a multifunctional fluid meter and to a method for measuring coolant, bio-diesel, gas-ethanol and diesel engine fluid (DEF), and to measure and report on the following properties:

A. For coolants: nitrite, the boiling point, and the freezing point.

B. Percent biodiesel in diesel fuel.

C. Percent DEF and percent urea in diesel engine fluid (DEF).

D. For gasoline containing ethanol, the percentage of ethanol.

The apparatus tests for qualitative and quantitative properties of the fluid under test by comparing test results to normal conditions. The apparatus then can determine the physical properties of the fluid being analyzed. The apparatus is an instrument that integrates two light sources within a spectrometer, each source being associated with a different optical path length. This dual path length design allows the apparatus to capture both NIR and UV spectral (300 nm-1100 nm) ranges.

An onboard computer controls the spectrometer and tabulates the results based on the data gathered. Software generates a report that includes the test results and a grading code. The code is a summary of the test results and gives an indication of the fluid properties.

The instrument features a broad-band optical spectrometer coupled to a custom sample compartment, a dedicated dual light source and an embedded data processing unit.

In accordance with the disclosure, an apparatus for analyzing a plurality of fluids, comprises a portion with an opening for receiving a fluid sample holder, the fluid sample holder having a fluid receiving portion of rectangular cross-section to define a first path for radiation of first wavelengths through fluid in the fluid receiving portion, and a second path for radiation of second wavelengths through fluid in the fluid receiving portion, the first path being shorter than the second path; a first source of radiation of the first wavelengths; a second source of radiation of the second wavelengths; a spectrometer for receiving the radiation of first wavelengths and the radiation of the second wavelengths after the radiation of the first wavelengths and the radiation of the second wavelengths have passed through the fluid and the fluid sample holder. The first wavelengths are shorter than the second wavelengths. The first wavelengths can be in a range of 200 nm to 750 nm and the second wavelengths can be in a range of 750 nm to 1100 nm.

The apparatus can further comprise a first set of optical elements for receiving and guiding the radiation of the first wavelengths to the spectrometer; and a second set of optical elements for receiving and guiding the radiation of the second wavelengths to the spectrometer.

The first source can be a deuterium lamp and the second source can be an incandescent tungsten lamp.

The apparatus can further comprisea database of properties of fluids to be analyzed by the apparatus, the properties being of the fluids in an unused state; and a processor for receiving an output of the spectrometer, processing the output to determine properties of the fluid being analyzed, and comparing the properties of the fluid being analyzed to properties of a corresponding fluid in an unused state, in the database. The processor can generate at least one diagnostic code based on the comparing of the properties of the fluid being analyzed to properties of a corresponding fluid in an unused state.

A memory can store a set of models, wherein the models provide rules for analyzing the fluids being analyzed.

In accordance with the disclosure, a method for analyzing a plurality of fluids, comprises: propagating along a first path, radiation of first wavelengths through a fluid, propagating along a second path radiation of second wavelengths through the fluid, the first path being shorter than the second path; receiving with a spectrometer the radiation of first wavelengths and the radiation of the second wavelengths after the radiation of the first wavelengths and the radiation of the second wavelengths propagates through the fluid; and analyzing the radiation of first wavelengths and the radiation of the second wavelengths to determine characteristics of the fluid.

The first wavelengths are shorter than the second wavelengths. The first wavelengths can be in a range of 200 nm to 750 nm and the second wavelengths can be in a range of 750 nm to 1100 nm.

The radiation of first wavelengths is a provided can be from a deuterium lamp and the second radiation of second wavelengths can be from an incandescent tungsten lamp.

The method further comprises processing an output of the spectrometer to determine properties of the fluid being analyzed; and comparing the properties of the fluid being analyzed to properties of a corresponding fluid in an unused state.

At least one diagnostic code based is generated by comparing of the properties of the fluid being analyzed to properties of a corresponding fluid in an unused state.

BRIEF DESCRIPTION OF THE DRAWINGS

The foregoing aspects and other features of the present disclosure are explained in the following description, taken in connection with the accompanying drawings, wherein.

DETAILED DESCRIPTION OF THE PREFERRED EMBODIMENTS

Figure 1:
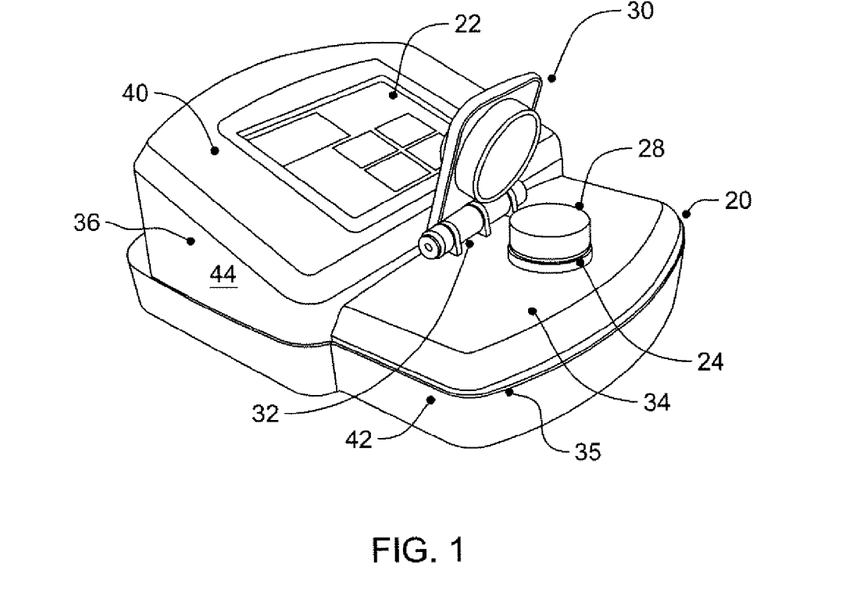
FIG. 1 is a perspective view of an embodiment of an apparatus for analyzing a fluid sample in accordance with the present disclosure.

Referring to FIG. 1, there is shown a perspective view of an apparatus incorporating features of the present disclosure. Although the apparatus will be described with reference to the embodiment shown in the drawings, it should be understood that the present disclosure can be embodied in many alternate forms of embodiments. In addition, any suitable size, shape or type of elements or materials could be used.

The instrument enclosure 20 is a molded plastic case that includes a user interface touch screen display 22, an opening 24 for receiving a sample container 26 (FIG. 2) with a container cover 28, and a sample chamber cover 30, which is hinged to enclosure 20 with hinge assembly 32. In use, sample chamber cover 30 is positioned directly over container cover 28 so that the sample container 26 is held in place, and stray light does not enter container 26.

Instrument enclosure 20 includes a first portion 34, which is substantially rectangular, with a curved front wall 35, in which largely the optical components of the apparatus are housed. A second portion 36 includes a sloping surface 40, having a window or opening therein for exposing the touch screen display 22. A bottom cover 42 is secured, preferably removeably, to a top portion 44 of enclosure 20. Second portion 36 houses largely the electronic components of the apparatus.

Figure 2:
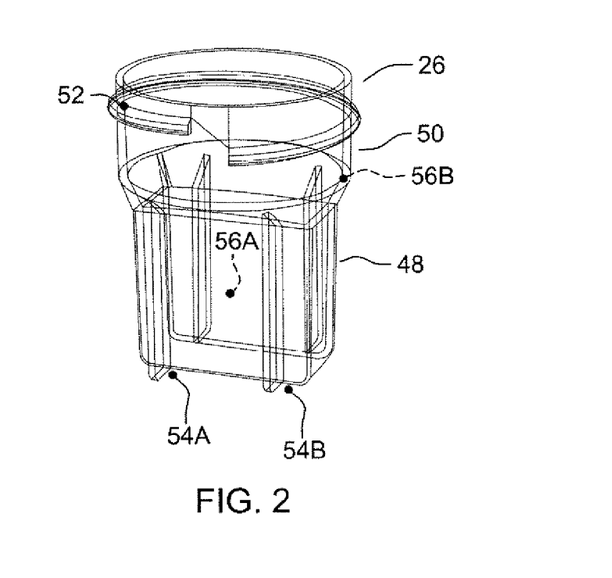
FIG. 2 is an embodiment of a dual path sample container for use in the apparatus of FIG. 1.

Referring to FIG. 2, a sample container 26, formed of a clear polymer, such as PMMA, or a clear optical grade acrylic is designed to be accepted within opening 24 (FIG. 1), includes a substantially rectangular sample cell region 48, and a substantially cylindrical top portion 50. Top portion 50 is configured with an external thread 52 for mating with an internal thread (not shown) of container cover 28, when container cover 28 is screwed on to sample container 26. Sample cell region 48 is configured with two parallel rectangular protrusions 54A and 54B on one of its larger surfaces, and with two parallel rectangular protrusions 56A and 56B on the other of its larger surfaces. The position of these rectangular protrusions is such that sample container 26 may be rotated by 180 degrees, and still be accepted within opening 24. The rectangular shape of sample cell region 48 provides two perpendicular paths of different lengths, both paths being perpendicular to the longitudinal axis of top portion 50, for the passage of light of different wavelengths therethrough, as more fully described below with respect to FIG. 3.

Figure 3:
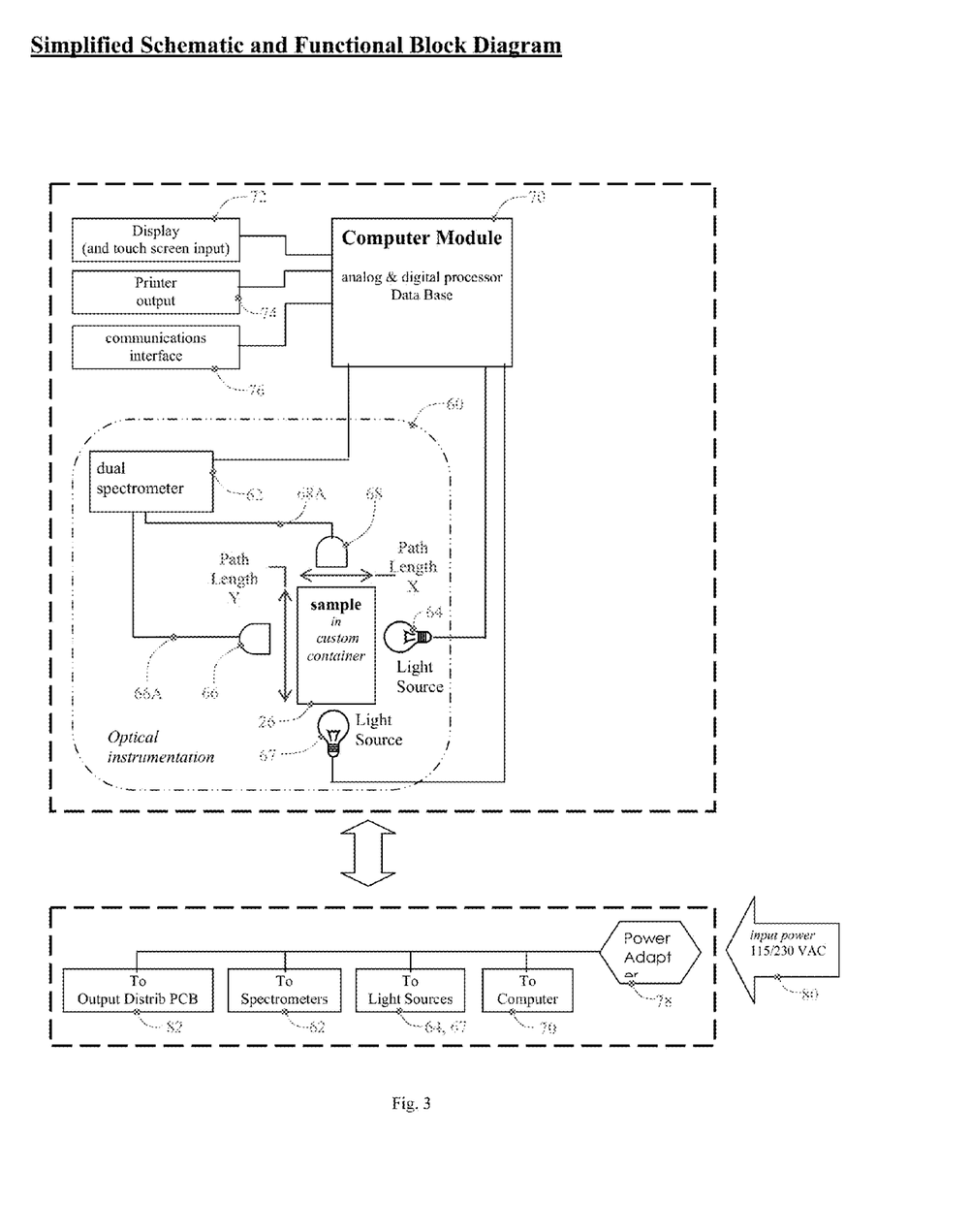
FIG. 3 is a simplified schematic and functional block diagram of the apparatus of FIG. 1.

FIG. 3 is a simplified schematic and functional block diagram of the apparatus within enclosure 20. The optical instrumentation 60 includes a dual spectrometer 62 configured with a broad-range diffraction grating (not shown), covering the range from 200 nm to 1100 nm. A first light source 64, which is preferably a deuterium source, provides illumination along a first sample path length of dimension X, which is the shorter path through the sample container 26. Light traveling through the sample container walls and the sample contained therein, generally in the wavelength range of 200 nm to 750 nm, arrives at a set of optics 66, which collects light, that is guided by a fiber optic cable 66A to detector 62. A second light source 67, which is preferably a tungsten light source, provides illumination along a second sample path length of dimension Y, which is the longer path through the sample container 26. Light traveling through the sample container walls and the sample contained therein, generally in the wavelength range of 750 nm to 1100 nm, illuminates a second set of optics 68, which collects light, that is guided by a fiber optic cable 68A to detector 62.

A computer module 70, which is preferably a dedicated industrial grade tablet PC with an embedded operating system, has associated therewith a touch-screen user display interface 72, a printer output 74 and external communications interface 76, for USB and Ethernet connections. Computer module 70 may include analog and digital processor or processors, and a database, used as described below. Preferably, the system is powered by a dedicated software package based on a touch screen/push button user interface. The system is based on a database driven operating environment. The output/results are delivered to the screen by display interface 72, and can be sent through the USB interface to an external printer. The fundamental properties of the used fluid to be analyzed is estimated from recorded spectral data from new (unused) and used fluid samples. The primary calculations for coolant fluid include the ethylene glycol content (and associated properties—freezing and boiling points), basic composition (coolant type—differentiating ELC blends), and certain inhibitors, as more fully described below.

A power adapter 78 having a 115/230 volt AC input 80 provides the various DC voltages required by a distributed circuit board 82, the dual spectrometer 62, light sources 64 and 67, and computer 70.

Figure 4:
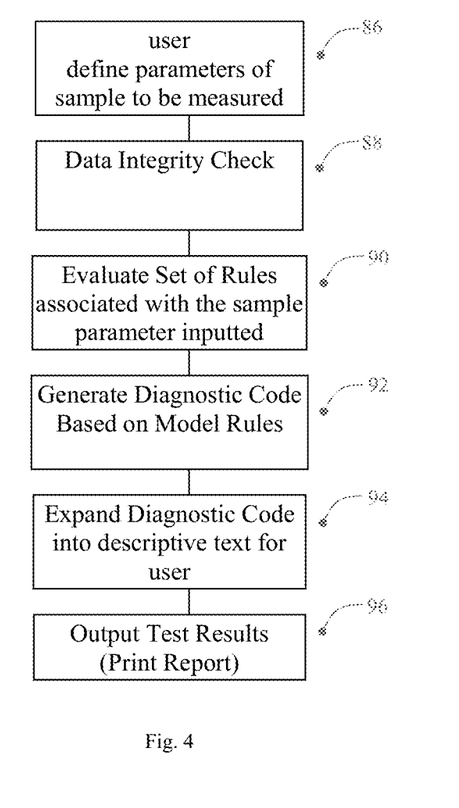
FIG. 4 is a high level system flow chart of the operation of the embodiment of FIG. 1.

FIG. 4 is a high level flow chart of the operation of an embodiment of an apparatus in accordance with the disclosure. At 86, the user defines parameters of the sample to be measured. A data integrity check is conducted at 88. At 90, rules associated with the sample parameter(s) inputted are evaluated. All the main calculations for glycol, DEF, fuels, etc. are carried out by multiple linear regression (MLR) or partial least squares (PLS) models. At 92, basic diagnostic codes are generated based on model rules. At 94, the diagnostic codes are expanded into descriptive text for display to a user. At 96, the test results may be outputted and a report printed on an attached printer.

Figure 5:
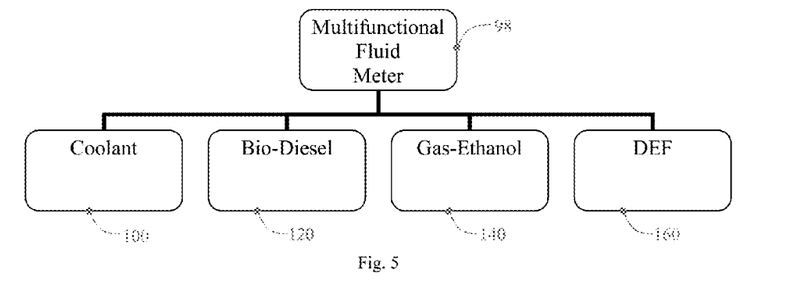
FIG. 5 is a logical illustration of the types of fluids that can be analyzed with the exemplary embodiment of FIG. 1.

FIG. 5 illustrates the basic multiple functionality, starting at a general display 98. The user is able to select the fluid to be analyzed as coolant 100, bio-diesel fuel 120, gas-ethanol mixtures 140 and DEF 160. After the selection is made, the flow charts of FIGS. 6, 7, 8 and 9, respectively, for the possible selections 100, 120, 140 and 160 are followed.

Figures 6, 7:
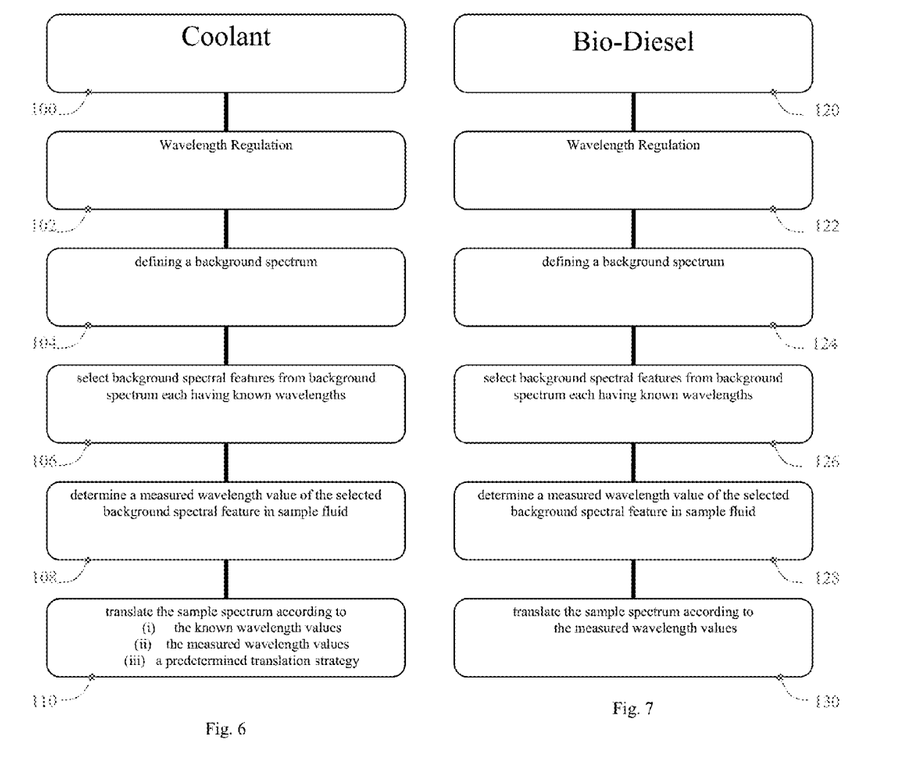
FIG. 6 is a flow chart of a series of steps that are performed for coolant analysis.
FIG. 7 is an example of a series of steps that are performed for bio-diesel fuel quality analysis.
Figure 8:
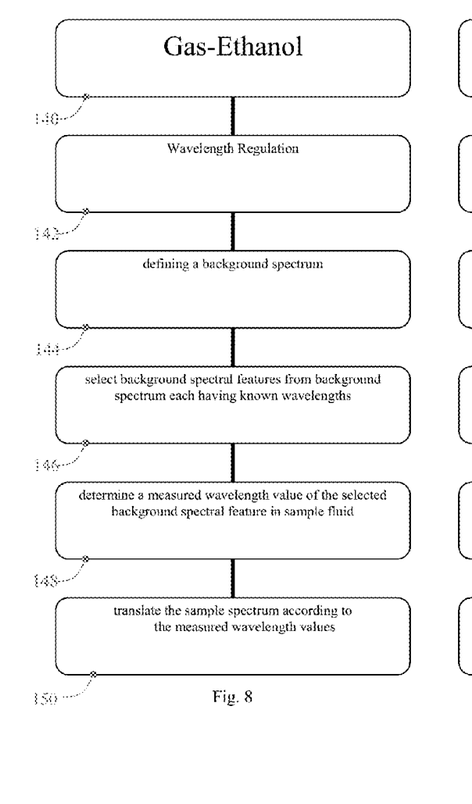
FIG. 8 is an example of a series of steps that are performed for Gas-ethanol fuel quality analysis.
Figure 9:
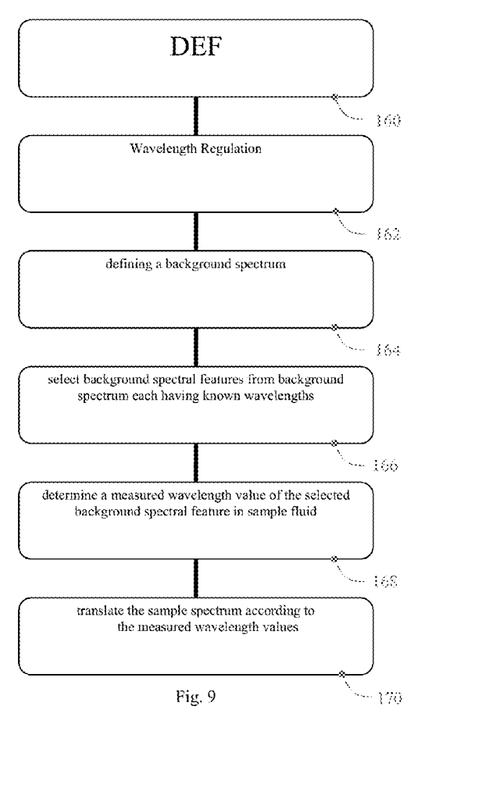
FIG. 9 is an example of a series of steps that performed for diesel exhaust fluid quality analysis.

The flowcharts of FIGS. 7, 8 and 9 are identical. However, the flowchart of FIG. 6 is described first, because it is different from those of FIGS. 7, 8 and 9 in the analysis conducted in the last step 110. Otherwise, the description relating to FIG. 6 below is identical to that for FIGS. 7, 8 and 9, wherein like last digits indicate identical steps.

A software model is used to calculate the concentrations of glycol, DEF, gas-ethanol, or biodiesel. Three different approaches or models, such as for example, those mentioned below, can be used for different ranges of wavelength within the overall spectrum. Then a polynomial (2nd or 3rd order) fit is applied to obtain what is considered to be the best overall fit for the spectrum. The coefficients are stored and used to do the final calculation on a specific instrument.

In the case of sample matching for type and color, a simple goodness of fit calculation, based on a vector calculation, is used.

For coolants, nitrite concentration is calculated from a highly overlapped absorption and the nitrite contribution is estimated by separating the absorption by means of a Saviitzky-Golay second derivative. The final value is computed from the span (Max-Min) of the derivative signature. A simple Beer's law computation is used for calculating the final result. A similar computation is used for the exclusion of the non-nitrite component.

In FIG. 6, when coolant is selected, regulation of wavelength provided by the sources occurs at 102. At 104, at predetermined, application driven intervals, a background calibration spectrum is established using an empty sample container (FIG. 2) in opening 24, as prompted by software. A background spectrum that was stored during the initial set-up of the instrument, is applied to this spectrum, and interpreted by the software to be the proper settings.

At 106, features in the background spectrum having known wavelengths are selected. At 108, a measured value of a selected background spectral feature of the sample fluid is determined. A sample container 26 is introduced into the opening 24. A UV-VIS light source is then turned on and the spectrum is acquired using the path-length setting based on the width of the sample container 26. This source is turned off and a second NIR light source is turned on and the second spectrum is added to the first using a longer path-length based on the width of the sample container 26. At 110, wavelength values of the sample spectrum are translated in accordance with the known wavelength values, the measured wavelength values, and a predetermined translation strategy. In this regard, reference is made to U.S. Pat. No. 6,707,043, wherein, as an example only, a method of regularizing a sample spectrum of a fluid sample is disclosed. The spectrum is then modeled against a large database set of known values to help determine certain results; other results are calculated by measuring certain areas of the spectral range and applying specific algorithms.

In steps 130, 150 and 170 of FIGS. 7, 8 and 9, respectively, it is only necessary to translate the sample spectrum in accordance with the measured wavelength values.

Figure 10:
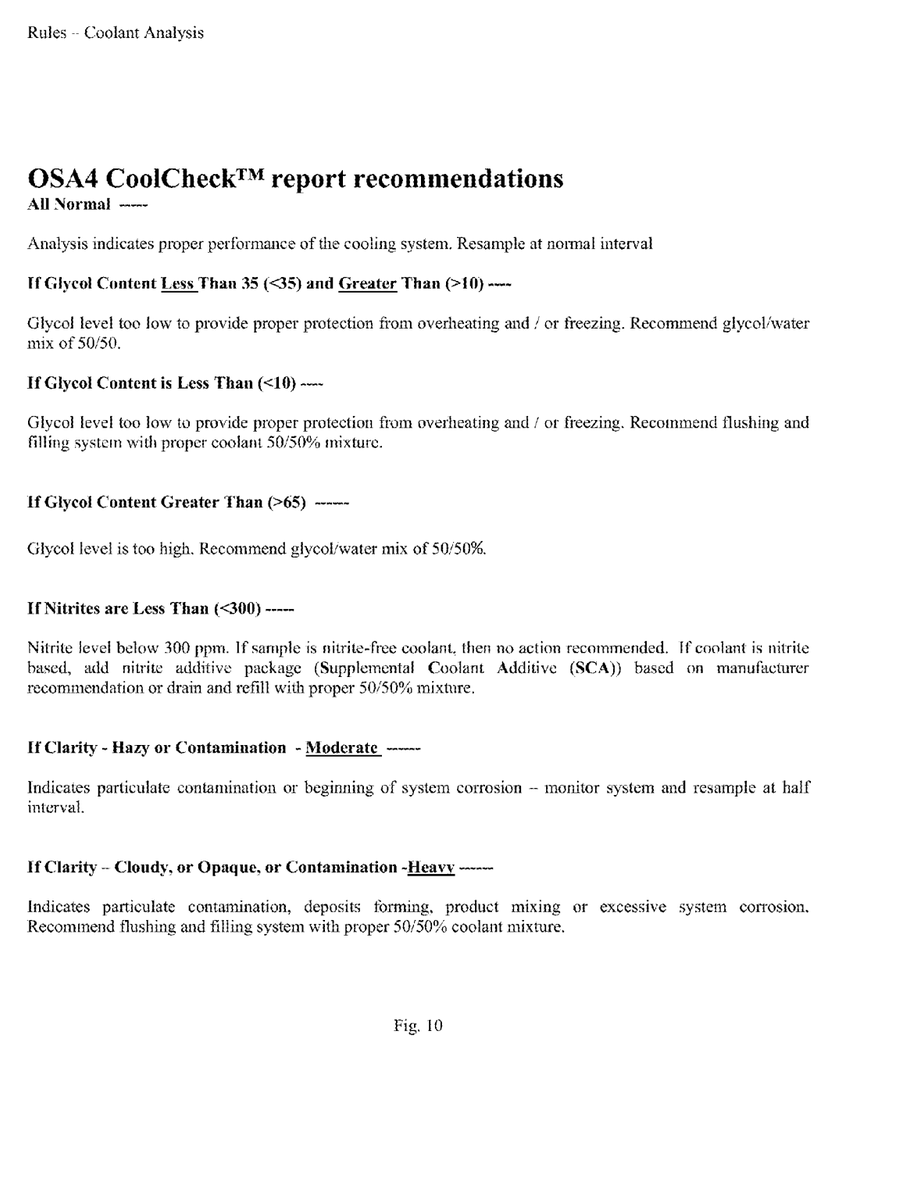
FIG. 10 illustrates a series of recommendations for a report on coolant propertied.

FIG. 10 includes report recommendation for various situations which may arise during an evaluation of a coolant sample. The recommendations are believed to be self-explanatory.

Figure 11:
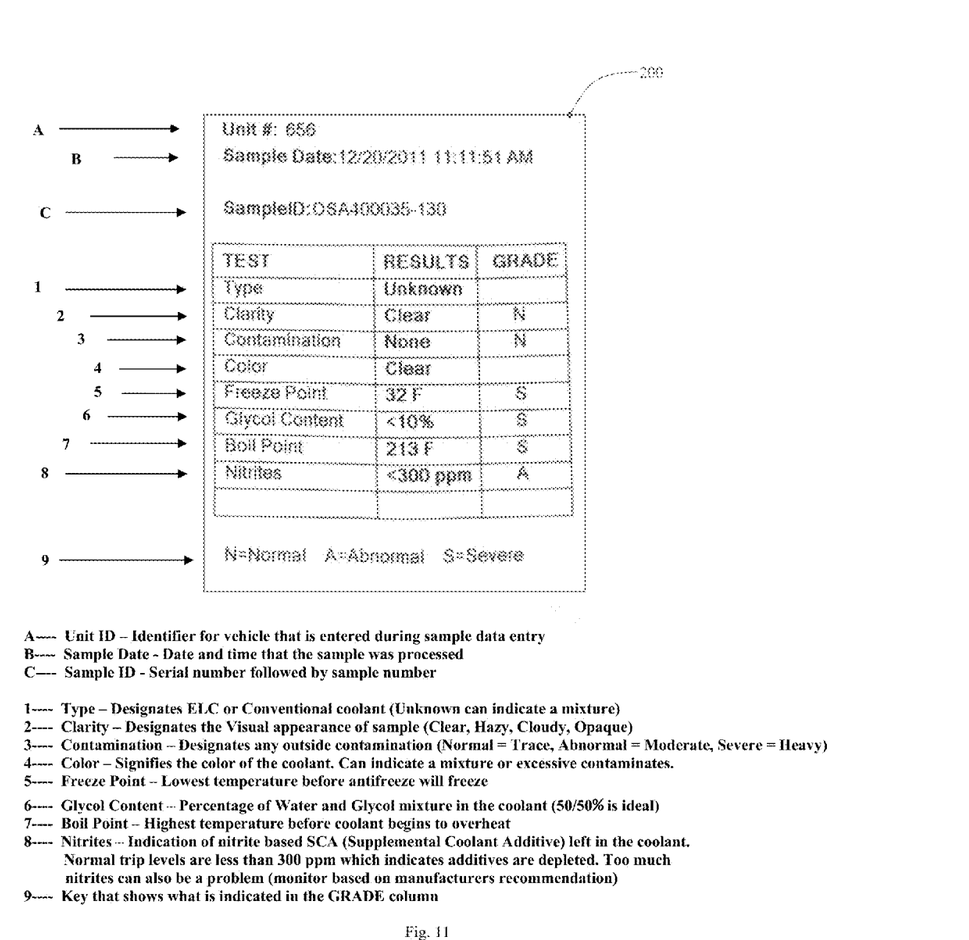
FIG. 11 is an example of a report, with explanatory notations, generated by the embodiment of the apparatus illustrated in FIG. 1.

FIG. 11 shows a typical report 200, and includes explanatory material for the items in the report. A report of this type can be shown on touch screen display 22. Again, this is believed to be self-explanatory.

It should be understood that the foregoing description is only illustrative of the disclosure. Various alternatives and modifications can be devised by those skilled in the art. Accordingly, the present disclosure is intended to embrace all such alternatives, modifications and variances.

What is claimed is:

1. An apparatus for analyzing a diesel exhaust fluid quality, comprising:
   a portion with an opening configured to receive a fluid sample holder, the fluid sample holder having a fluid receiving portion, the fluid sample holder including a sample cell region of rectangular cross-section to define a first dimension for a first path for radiation of first wavelengths through diesel exhaust fluid in the sample cell region and a second dimension longer than and perpendicular to the first dimension to define a second path for radiation of second wavelengths through diesel exhaust fluid in the sample cell region, the first path being shorter than the second path;

a first source of radiation of the first wavelengths;

a second source for radiation of the second wavelengths;

a dual path length spectrometer for receiving collected radiation of the first wavelengths and collected radiation of the second wavelengths after the radiation of the first wavelengths and the radiation of the second wavelengths have passed through the diesel exhaust fluid in the sample cell region;

a database of properties of diesel exhaust fluid in an unused state; and a processor for receiving an output of the spectrometer, processing the output to determine properties of the diesel exhaust fluid being analyzed, and comparing the properties of the diesel exhaust fluid being analyzed to properties of the diesel exhaust fluid in an unused state in the database.

2. The apparatus of claim 1 wherein the first wavelengths are in a range of 200 nm to 750 nm and the second wavelengths are in a range of 750 nm to 1100 nm.

3. The apparatus of claim 1 wherein the first source is a deuterium lamp and the second source is an incandescent tungsten lamp.

4. A method for analyzing diesel exhaust fluid quality, comprising:

propagating along a first path through a fluid sample holder including a rectangular cross-section sample cell region defining a first dimension for the first path, radiation of first wavelengths through a diesel exhaust fluid;

propagating along a second path through a second dimension of the sample cell region which is longer than and perpendicular to the first dimension defining the second path, radiation of second wavelengths through the diesel exhaust fluid, the first path being shorter than the second path;

receiving with a dual path length spectrometer collected radiation of the first wavelengths and collected radiation of the second wavelengths after the radiation of the first wavelengths and the radiation of the second wavelengths propagates through the diesel exhaust fluid; and analyzing the radiation of first wavelengths and the radiation of the second wavelengths to determine characteristics of the diesel exhaust fluid;

processing an output of the spectrometer to determine properties of the diesel exhaust fluid being analyzed; and comparing the properties of the diesel exhaust fluid being analyzed to properties of a diesel exhaust fluid in an unused state.

5. An apparatus for analyzing a plurality of fluids, comprising;

a portion with an opening configured to receive a fluid sample holder, the fluid sample holder having a fluid receiving portion, the fluid sample holder including a sample cell region of rectangular cross-section to define a first path for radiation of first wavelengths through fluid in the sample cell region and a second dimension longer than and perpendicular to the first dimension to define a second path for radiation of second wavelengths through fluid in the sample cell region, the first path being shorter than the second path;

a first source of radiation of the first wavelengths;

a second source for radiation of the second wavelengths;

a dual path length spectrometer for receiving collected radiation of first wavelengths and collected radiation of the second wavelengths after the radiation of the first wavelengths and the radiation of the second wavelengths have passed through the fluid and the sample cell region;

a database of qualitative, quantitative, and physical properties of fluids to be analyzed by the apparatus, the properties being of the fluids in an unused state; and a processor for receiving an output of the spectrometer, processing the output to determine qualitative, quantitative, and physical properties of the fluid being analyzed, and comparing the qualitative, quantitative, and physical properties of the fluid being analyzed to qualitative, quantitative, and physical properties of a corresponding fluid in an unused state, in the database, wherein the fluids to be analyzed include engine coolant, bio-diesel fuel, gasoline-ethanol mixtures, and diesel exhaust fluid.

6. A method for analyzing a plurality of fluids, comprising:

propagating along a first path through a fluid sample holder including a rectangular cross-section sample cell region defining the first path, radiation of first wavelengths through a fluid, propagating along a second path through a second dimension of the sample cell region which is longer than and perpendicular to the first dimension defining the second path, radiation of second wavelengths through the fluid, the first path being shorter than the second path;

receiving with a dual path length spectrometer collected radiation of first wavelengths and collected radiation of the second wavelengths after the radiation of the first wavelengths and the radiation of the second wavelengths propagates through the fluid;

analyzing the radiation of first wavelengths and the radiation of the second wavelengths to determine characteristics of the fluid; and processing an output of the spectrometer to determine qualitative, quantitative, and physical properties of the fluid being analyzed; and comparing the qualitative, quantitative, and physical properties of the fluid being analyzed to qualitative, quantitative, and physical properties of a corresponding fluid in an unused state;

wherein the fluids to be analyzed include engine coolant, bio-diesel fuel, gasoline-ethanol mixtures, and diesel exhaust fluid.

7. An apparatus for analyzing a plurality of fluids, comprising:

a sample container including a substantially cylindrical top portion configured to receive a sample fluid and a substantially rectangular cross-section sample cell region for holding the sample fluid, the rectangular cross-section defining a first dimension for a first path for radiation of first wavelengths through the sample fluid in the sample cell region and a second dimension longer than the first dimension defining a second path perpendicular to the first path for radiation of second wavelengths through the sample fluid in the sample cell region, the first path being shorter than the second path;

a first source of radiation of the first wavelengths;

a second source for radiation of the second wavelengths;

a dual path length spectrometer for receiving collected radiation of first wavelengths and collected radiation of the second wavelengths after the radiation of the first wavelengths and the radiation of the second wavelengths have passed through the sample fluid and the sample cell region;

a database of properties of fluid in an unused state; and a processor for receiving output of the spectrometer, processing the output to determine properties of the sample fluid, and comparing properties of the fluid in an unused state from the database to the properties of the sample fluid, wherein the fluids to be analyzed include engine coolant, bio-diesel fuel, gasoline-ethanol mixtures, and diesel exhaust fluid.

8. The apparatus of claim 7 in which the top portion includes threads.

9. The apparatus of claim 7 in which both paths are perpendicular to a longitudinal axis of the top portion.

\* \* \* \* \*